(12) United States Patent
Mandrusov et al.

(10) Patent No.: US 6,660,034 B1
(45) Date of Patent: Dec. 9, 2003

(54) STENT FOR INCREASING BLOOD FLOW TO ISCHEMIC TISSUES AND A METHOD OF USING THE SAME

(75) Inventors: Evgenia Mandrusov, Campbell, CA (US); Paul Consigny, Morgan Hill, CA (US); Syed Faiyaz Ahmed Hossainy, Fremont, CA (US); Dary Mirzaee, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 131 days.

(21) Appl. No.: 09/846,498

(22) Filed: Apr. 30, 2001

(51) Int. Cl.$^7$ .................................................. A61F 2/06
(52) U.S. Cl. .................................................... 623/1.42
(58) Field of Search ........................... 623/1.15, 1.13, 623/1.41, 1.42, 1.43, 1.44, 1.45, 1.46, 1.47, 1.48

(56) References Cited

U.S. PATENT DOCUMENTS

| | | | | |
|---|---|---|---|---|
| 6,071,305 A | * | 6/2000 | Brown et al. | 623/1.42 |
| 6,206,914 B1 | * | 3/2001 | Soykan et al. | 623/1.42 |
| 6,299,604 B1 | * | 10/2001 | Ragheb et al. | 604/265 |
| 6,334,872 B1 | * | 1/2002 | Termin et al. | 623/1.38 |
| 6,379,379 B1 | * | 4/2002 | Wang | 623/1.15 |
| 6,391,052 B2 | * | 5/2002 | Buirge et al. | 623/1.47 |
| 6,395,023 B1 | * | 5/2002 | Summers | 623/1.44 |
| 6,436,135 B1 | * | 8/2002 | Goldfarb | 623/1.39 |

OTHER PUBLICATIONS

Heeschen et al., *Nicotine Stimulates Tumor Angiogenesis*, Abstract, American College of Cardiology 50th Annual Scientific Session, Stanford, California, Mar. 18, 2001.

Penta et al., *Del1 Induces Integrin Signaling and Angiogenesis by Ligation of αVβ3*, J. Biolog. Chem. 274(16):11101–11109 (Apr. 16, 1999).

I. Buschmann, et al., "Arteriogenesis Versus Angiogenesis: Two Mechanisms of Vessel Growth," News Physiol. Sci., vol. 14, pp. 121–125 (Jun. 1999).

A. Helisch, et al., "Angiogenesis and arteriogenesis—not yet for prescription," Z Kardiol, 89, pp. 239–244 (2000).

W.D. Ito, et al., "Monocyte Chemotactic Protein–1 Increases Collateral and Peripheral Conductance After Femoral Artery Occlusion," Circulation Research, vol. 80, No. 6, pp. 829–837 (Jun. 1997).

N. Kipshidze, et al., "Therapeutic Angiogenesis for Critical Limb Ischemia to Limit or Avoid Amputation," The Journal of Invasive Cardiology, vol. 11, No. 1, pp. 25–28 (Jan. 1999).

B.D. Klugherz, et al., "Gene delivery from a DNA controlled–release stent in porcine coronary arteries," Nature Biotechnology, vol. 18, pp. 1181–1184 (Nov. 2000).

J. Li, et al., "PR39, a peptide regulator of angiogenesis," Nature Medicine, vol. 6, No. 1, pp. 49–55 (Jan. 2000).

M. Simons, et al., "Clinical Trials in Coronary Angiogenesis: Issues, Problems, Consensus. An Expert Panel Summary," Circulation, pp. 1–14, (Sep. 2000).

W. Zheng, et al., "Mechanisms of coronary angiogenesis in response to stretch: role of VEGF and TGF–beta," AJP—Heart and Circulatory Physiology, vol. 280, Issue 2, H909–H917, (Feb. 2001).

* cited by examiner

*Primary Examiner*—Corrine McDermott
*Assistant Examiner*—Alvin Stewart
(74) *Attorney, Agent, or Firm*—Squire, Sanders & Dempsey, L.L.P.

(57) ABSTRACT

An implantable stent for a vessel includes a tubular body having an inner and outer surface. The inner and outer surfaces are coated with therapeutic substances. The therapeutic substance of the inner surface, such as an angiogenic substance, can be released downstream in the lumen. The therapeutic substance of the outer surface can be applied to the inner surface of the vessel.

28 Claims, 2 Drawing Sheets

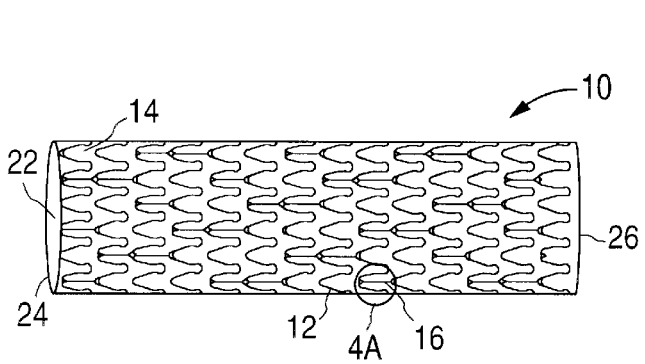
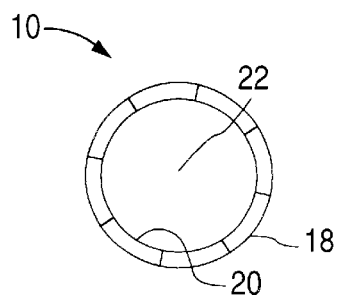
FIGURE 1A     FIGURE 1B
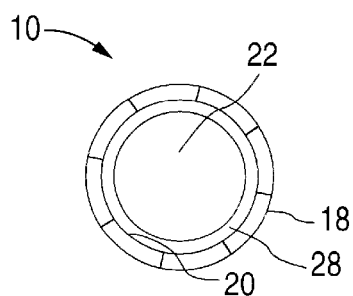
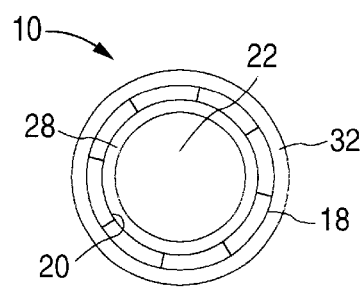
FIGURE 2     FIGURE 3
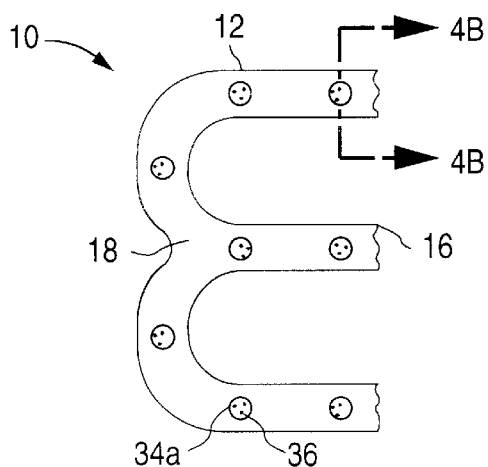
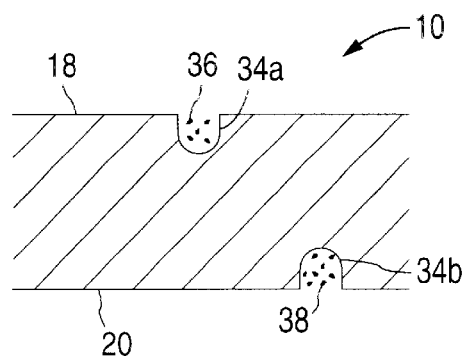
FIGURE 4A     FIGURE 4B

STENT FOR INCREASING BLOOD FLOW TO ISCHEMIC TISSUES AND A METHOD OF USING THE SAME

BACKGROUND OF THE INVENTION

1. Field of the Invention

This invention relates to implantable medical devices, such as stents, and a method of resolving ischemia by inducing formation of new blood vessels through angiogenesis and arteriogenesis.

2. Description of the Background

A major component of morbidity and mortality attributable to cardiovascular disease occurs as a consequence of the partial or complete blockage of vessels carrying blood in the coronary and/or peripheral vasculature. When such vessels are occluded, various complications may result from death of tissue previously nourished by the occluded vessels or inability of the occluded vessels to transport sufficient blood supply to regions requiring high blood consumption and accompanying nutrients.

Blood vessel occlusions are commonly treated by mechanically enhancing blood flow in the affected vessels. Such mechanical enhancements are often provided by employing surgical techniques that attach natural or synthetic conduits proximal and distal to the areas of occlusion, thereby providing bypass grafts, or revascularization by various means to physically enlarge the vascular lumen at the site of occlusion. These revascularization procedures involve such devices as balloons, endovascular knives (atherectomy), and endovascular drills. The surgical approach is accompanied by significant morbidity and even mortality, while the angioplasty-type processes are complicated by recurrent stenoses in many cases.

In some individuals, blood vessel occlusion is partially compensated by the natural process of therapeutic angiogenesis, in which new vessels are formed to replace the function of the impaired vessels. These new conduits may facilitate restoration of blood flow to the deprived tissue, thereby constituting "natural bypasses" around the occluded vessels. However, some individuals are unable to generate sufficient new vessels to adequately compensate for the diminished blood flow caused by cardiovascular disease. Accordingly, it would be desirable to provide methods and systems for delivering agents to help stimulate the natural process of therapeutic angiogenesis in occluded coronary and peripheral arteries in order to treat ischemia.

SUMMARY

A stent is provided. The stent includes a tubular body having an outer surface for contacting the wall of a vessel and an inner surface. The stent also includes a first coating supported by the inner surface and containing an angiogenic substance for the release of the angiogenic substance in the vessel. In addition, the stent includes a second coating supported by the outer surface and containing a therapeutic substance for applying the therapeutic substance to the wall of the vessel.

In some embodiments, the therapeutic substance is selected from antiproliferative, antineoplastic, antiinflammatory, antiplatelet, anticoagulant, antifibrin, antithrombin, antimitotic, antibiotic, antioxidant, and antimigratory substances, inhibitors of matrix synthesis, and combinations thereof.

Also provided is a stent, which includes a tubular structure having an inner surface and an outer surface, for implanting in a blood vessel. The stent includes a first therapeutic substance carried by the inner surface for being released downstream with the flow of blood and a second therapeutic substance, which is different from the first therapeutic substance, carried by the outer surface for application to the blood vessel wall. The first therapeutic substance facilitates therapeutic angiogenesis, and the second therapeutic substance inhibits migration or proliferation of smooth muscle cells.

In one embodiment, the inner surface of the stent includes a plurality of cavities for releasing the first therapeutic substance when exposed to the flow of blood. In another embodiment, the inner surface includes a plurality of cavities for releasing the first therapeutic substance when exposed to the flow of blood, and the outer surface includes a plurality of cavities for applying the second therapeutic substance to the blood vessel wall.

A method for increasing blood flow to ischemic tissues located downstream from an occluded region in a blood vessel is also provided. The method includes implanting a stent in the blood vessel at a location upstream from the ischemic tissues. The stent has an inner surface carrying an angiogenic substance.

In one embodiment, the stent is positioned at a location upstream of the occluded region. In another embodiment, the stent is positioned across at least a portion of the occluded region.

In yet another embodiment, the stent additionally includes a coating disposed on the outer surface of the stent. The coating includes a therapeutic substance. In another embodiment, the stent includes cavities on the outer surface containing a therapeutic substance.

BRIEF DESCRIPTION OF THE FIGURES

FIG. 1A illustrates a stent.

FIG. 1B illustrates an end view of the stent of FIG. 1A.

FIG. 2 illustrates the stent of FIG. 1B having a first coating containing an angiogenic substance formed on the inner surface.

FIG. 3 illustrates the stent of FIG. 2 having a second coating formed on the outer surface.

FIG. 4A is the region 4A of the stent of FIG. 1A illustrating a therapeutic substance in cavities formed within the outer surface.

FIG. 4B illustrates the stent of FIG. 4A taken along line 4B—4B in accordance with an embodiment in which the therapeutic substances are releasably contained in cavities within the inner and outer surfaces, respectively.

DETAILED DESCRIPTION

Figure 5A:
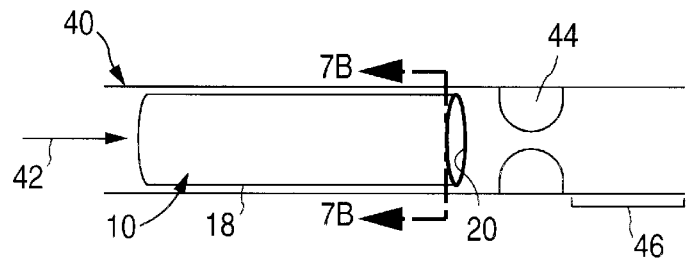
FIGS. 5A–5D illustrate a method for increasing blood flow to ischemic tissue in accordance with several embodiments of the present invention.
Figure 5B:
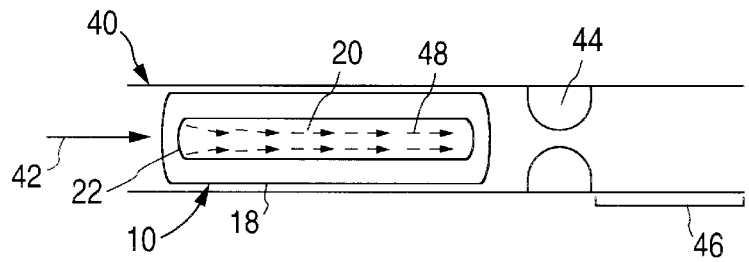
Figure 5C:
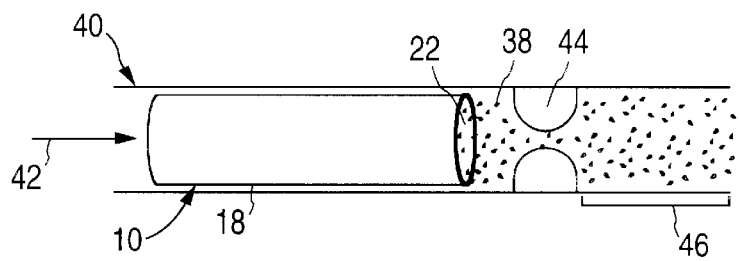

Angiogenic substances should be understood to broadly include any proteins, peptides, and small molecules as well as cells, genes, and other substances that promote, stimulate or cause therapeutic angiogenesis. One of ordinary skill in the art is familiar with methods used to determine the angiogenic or arteriogenic activity of a substance, examples of which include the use of rabbit hind limb ischemia models and pig ameroid constrictor models. Representative examples of angiogenic substances include vascular endothelial growth factor (VEGF) in any of its multiple isoforms, fibroblast growth factors, monocyte chemoattractant protein 1 (MCP-1), transforming growth factor beta (TGF-beta) in any of its multiple isoforms, transforming growth factor alpha (TGF-alpha), lipid factors, hypoxia-inducible factor 1-alpha (HIF-1-alpha), PR39, del 1, nicotine, insulin-like growth factors, placental growth factor (PIGF), hepatocyte growth factor (HGF), estrogen, follistatin, proliferin, prostaglandin E1, prostaglandin E2, cytokines, tumor necrosis factor (TNF-alpha), erythropoietin, granulocyte colony-stimulating factor (G-CSF), granulocyte macrophage colony-stimulating factor (GM-CSF), angiogenin, hormones, and genes that encode such substances.

VEGF, a 46 kD protein, has isoforms containing 121, 165, 189, and 206 amino acids. VEGF is a heparin-binding protein that is mitogenic for endothelial cells only. This mitogen is also known as vascular permeability factor and will induce vessel leakage at doses higher than those required for angiogenic response. VEGF has been shown to induce functionally significant angiogenesis in the acute and chronic coronary ischemia models in pigs and dogs. This protein was tested in phase II clinical trials and was shown to be safe at the administered doses.

The heparin-binding fibroblast growth factor (FGF) family includes ten currently identified mitogens and four additional homologs of unknown function. FGF-2, also referred to as FGF-beta, is a 16.5 kD, 146 amino acid protein. FGF-2 is a pluripotent mitogen capable of stimulating migration and proliferation of a variety of cell types including fibroblasts, macrophages, smooth muscle cells and endothelial cells. FGF-2 can also stimulate endothelial production of various proteases including plasminogen activator and matrix metalloproteinases, induce significant vasodilation through stimulation of nitric oxide release, and promote chemotaxis. FGF-2 is present in the normal myocardium and its expression is potentiated by hypoxia or hemodynamic stress. This protein has been shown to induce functionally significant angiogenesis in the acute and chronic coronary ischemia models in pigs and dogs. FGF-2 was tested in phase II clinical trials and was shown to be safe at the administered doses. FGF-1, also referred to as FGF-alpha, is an unstable form of fibroblast growth factor that has similar action as FGF-2. However, FGF-1is 30–100 times less potent than FGF-2.

MCP-1 is produced by shear stress-activated endothelium. Monocytes transmigrate through the vessel wall of proliferating collateral arteries and produce MCP-1, resulting in monocyte homing and acceleration of the natural process of collateral growth by degradation of the basement membrane, proliferation of smooth muscle cells and endothelial cells, and enlargement of the pre-existing vessel.

TGF-beta exists in at least five isoforms, each of which is encoded by a different gene. TGF-beta directly induces proliferation, migration and/or differentiation of endothelial cells. It has been reported that TGF-beta signaling may regulate VEGF expression in cardiac myocytes. (Zheng, et al., "Mechanisms of coronary angiogenesis in response to stretch: role of VEGF and TGF-beta," Am J. Physiol Heart Circ. Physiol, 280(2):H909–17 (February 2001).)

TGF-alpha directly induces proliferation, migration and/ or differentiation of endothelial cells.

Lipid factors include spingosine 1-phosphate (SIP), which is stored in platelet granules and is released upon platelet activation, as well as lysophasphatidate (LPA) and phosphatidic acid (PA). SIP, LPA, and PA bind to endothelial differentiation gene receptors, a novel family of G-protein-coupled receptors present in endothelial cells. When stimulated, these receptors activate pathways that ultimately result in endothelial cell responses associated with angiogenesis including the liberation of endothelial cells from established monolayers, chemotactic migration, and proliferation.

HIF-1-alpha has been shown in cell culture to be a transcriptional activator for VEGF. HIF-1-alpha has been selectively expressed in areas of ischemia or infarction, but not in myocardium remote to ischemic or infarcted areas. The presence of HIF-1-alpha MRNA, and subsequently the presence of VEGF mRNA, in the heart tissue of patients with infarction is said to indicate that HIF-1-alpha contributes to limitation of infarct size by promoting angiogenesis and vascular remodeling, and that it does so by increasing steady-state levels of VEGF mRNA.

PR39, a macrophage-derived peptide, inhibits the ubiquitin-proteasome-dependent degradation of HIF-1-alpha protein, resulting in accelerated formation of vascular structures in vitro and increased myocardial vasculature in mice. Coronary flow studies in mice have demonstrated that PR39-induced angiogenesis resulted in the production of functional blood vessels. Such findings indicate that PR39 and related compounds can be used as potent inductors of angiogenesis and that selective inhibition of HIF-1-alpha degradation may underlie the mechanism of inflammation-induced angiogenesis. (Li, et al., "A peptide regulator of angiogenesis," Nat Med. 6(1), 6(3), pgs. 49–55 (January and March 2000))

Del 1, an extracellular matrix protein, encodes three Notch-like epidermal growth factor repeats: an RGD motif, and two discoidin domains. Del 1 is expressed in an endothelial cell-restricted pattern during early development. In some studies, recombinant baculovirus Del 1 protein was shown to promote alphavbeta3-dependent endothelial cell attachment and migration. Attachment of endothelial cells to Del 1 was associated with clustering of alphavbeta3, the formation of focal complexes, and recruitment of talin and vinculin into these complexes. These events were shown to be associated with phosphorylation of proteins in the focal complexes, including the time-dependent phosphorylation of p125(FAK), MAPK, and Shc. When recombinant Del 1 was evaluated in an in-ovo chick chorioallantoic membrane assay, it was found to have potent angiogenic activity. This angiogenic activity was inhibited by a monoclonal antibody directed against alphavbeta3, and an RAD mutant Del 1 protein was inactive. Thus, Del 1 has been indicated to provide a unique autocrine angiogenic pathway for the embryonic endothelium, and this function is mediated in part by productive ligation of integrin alphabeta3. (Penta, et al., "Del 1 induces integrin signaling and angiogenesis by ligation of alphaVbeta3," J. Biol Chem, 16; 274 (April 1999).)

Nicotine, via stimulation of nicotinic receptors, has been shown to enhance angiogenesis and may stimulate tumor growth in part by enhancing tumor vascularity. (Heeschen, et al., "Nicotine Stimulates Tumor Angiogenesis," Stanford University, Stanford, Calif., (2001).)

Two different insulin-like growth factors have been described, IGF-1 and IGF-2. The two factors are encoded by two different genes, which are expressed differentially in different tissues and at different times of development. IGF-1 is a 150 kD peptide that is synthesized by many cell types, including smooth muscle cells. This peptide stimulates migration and tube formation by vascular endothelial cells as wells as migration and proliferation of smooth muscle cells, which are important steps in the angiogenesis process.

"Therapeutic angiogenesis" refers to the processes of causing or inducing angiogenesis and arteriogenesis.

"Angiogenesis" is defined as promotion or causation of the formation of new blood vessels.

"Arteriogenesis" is the formation of collateral vessels, which typically occurs in a non-ischemic region of a vessel. The collateral vessels allow blood to flow from a well-perfused region of the vessel into the ischemic region.

"Ischemia" is defined as localized reduction in blood flow caused by narrowing or occlusion of one or more vessels, such as coronary arteries or their branches, most often through thrombosis or via deposits of fat, connective tissue, calcification of the walls, or restenosis caused by the abnormal migration and proliferation of smooth muscle cells.

"Occlusion" is defined as the total or partial obstruction of blood flow through a vessel.

"Smooth muscle cells" include those cells derived from the medial and adventitial layers of the vessel that migrate and proliferate in intimal vascular sites.

"Migration" of smooth muscle cells means movement of these cells in vivo from the medial layers of a vessel into the intima, such as may also be studied in vitro by following the motion of a cell from one location to another, e.g., using time-lapse cinematography or a video recorder and manual counting of smooth muscle cell migration out of a defined area in the tissue culture over time.

"Proliferation" of smooth muscle cells means increase in cell number.

"Abnormal" proliferation means division, growth or migration of cells occurring more rapidly or to a significantly greater extent than typically occurs in a normally functioning cell of the same type, i.e., hyper-proliferation.

"Inhibiting" cellular activity means reducing, delaying or eliminating smooth muscle cell migration and/or proliferation that causes hyperplasia, restenosis, and vascular occlusions, particularly following biologically or mechanically mediated vascular injury or trauma or under conditions that would predispose a mammal to suffer such a vascular injury or trauma.

A stent is broadly defined to include any inter- or intraluminal device used for the release of an active ingredient and/or for upholding the luminal patency. Examples of stents include self-expandable stents, balloon-expandable stents, and stent-grafts. The stent can be made of a metallic material or an alloy such as, but not limited to, stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. The stent can also be made from bioabsorbable or biostable polymers.

The stent can be coated with a polymeric material for the delivery of the angiogenic substance alone or in combination with a therapeutic substance. "Polymer," "poly," and "polymeric" are defined as compounds that are the product of a polymerization reaction and are inclusive of homopolymers, copolymers, terpolymers etc., including random, alternating, block, and graft variations thereof. Representative examples of polymers that can be used with the embodiments of the present invention include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly (hydroxybutyrate); poly(hydroxybutyrate-co-valerate); polydioxanone; polyorthoester; polyanhydride; poly (glycolic acid); poly(D,L-lactic acid); poly(glycolic acid-co-trimethylene carbonate); polyphosphoester; polyphosphoester urethane; poly(amino acids); cyanoacrylates; poly (trimethylene carbonate); poly(iminocarbonate); copoly (ether-esters) (e.g. PEO/PLA); polyalkylene oxalates; polyphosphazenes and biomolecules such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

The Figures have not been drawn to scale, and the dimensions such as depth and thickness of the various regions and layers have been over or under emphasized for illustrative purposes. Referring to FIGS. 1A and 1B, a stent 10 is formed from a plurality of struts 12. Struts 12 are separated by gaps 14 and may be interconnected by connecting elements 16. Struts 12 can be connected in any suitable configuration and pattern. Stent 10 is illustrated having an outer surface 18 (tissue-contacting surface) and an inner surface 20 (blood-contacting surface). A hollow, central bore 22 extends longitudinally from a first end 24 to a second end 26 of stent 10.

FIG. 2 illustrates stent 10 having a first coating 28 formed on inner surface 20. First coating 28 can be of any suitable thickness. The thickness of first coating 28 can be from about 0.1–15 microns, more narrowly from about 3 microns to about 8 microns. By way of example, first coating 28 can have a thickness of about 5 microns.

First coating 28 can be made from a polymeric material containing an angiogenic substance. First coating 28 can be formed by any suitable method, such as by applying a first solution containing a dissolved mixture of a first solvent, a first polymer, and the angiogenic substance onto inner surface 20 and allowing the first solvent to evaporate from the first solution. Examples of suitable solvents include dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

The first solution can be deposited onto inner surface 20 in any suitable manner capable of allowing the first solution to be applied to inner surface 20 without exposure of outer surface 18 to the first solution. For example, outer surface 18 can be covered by a removable sheath during application of the first solution, allowing the first solution to coat only inner surface 20.

The dosage or concentration of the angiogenic substance required to produce a therapeutic effect should be less than the level at which the angiogenic substance produces toxic effects and greater than the level at which non-therapeutic results are obtained. The dosage or concentration of the angiogenic substance required can depend upon factors such as the particular circumstances of the patient; the time over which the angiogenic substance administered resides at the treatment site; and if other bioactive substances are employed, the nature and type of the substance or combination of substances. Standard pharmacological test procedures to determine dosages are understood by one of ordinary skill in the art.

FIG. 3 illustrates stent 10 coated in accordance with another embodiment of the present invention. In addition to first coating 28 containing an angiogenic substance on inner surface 20, a second coating 32 containing a therapeutic substance is formed on outer surface 18 of stent 10. Second coating 32 can be of any suitable thickness. The thickness of second coating 32 can be from about 0.1–15 microns, more narrowly from about 3 microns to about 8 microns. By way of example, second coating 32 can have a thickness of about 4 microns.

Second coating 32 can be formed on outer surface 18 prior to or subsequent to the formation of first coating 28 on inner surface 20. Stent 10 can be temporarily mounted on a conventional mandrel such that the mandrel fits within hollow bore 22 and against inner surface 20 or first coating 28. Stent 10 can then be immersed in or sprayed with a polymer-solvent composition containing a therapeutic substance to form second coating 32.

The therapeutic substance in second coating 32 can be an angiogenic substance that is the same as or different than the angiogenic substance contained within first coating 28. Alternatively, the therapeutic substance in second coating 32 can be any active ingredient capable of exerting a therapeutic or prophylactic effect in the practice of the present invention. The therapeutic substance can also be for enhancing wound healing in a vascular site and improving the structural and elastic properties of the vascular site. More particularly, the therapeutic substance should be for inhibiting abnormal migration and/or proliferation of smooth muscle cells for the treatment of restenosis. Examples of such substances include antiproliferative, antineoplastic, antiinflammatory, antiplatelet, anticoagulant, antifibrin, antithrombin, antimitotic, antibiotic, antioxidant and antimigratory substances, inhibitors of matrix synthesis, and combinations thereof.

A suitable example of an antiproliferative substance is actinomycin D, or derivatives and analogs thereof. Synonyms of actinomycin D include dactinomycin, actinomycin IV, actinomycin $I_1$, actinomycin $X_1$, and actinomycin $C_1$. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E3B® (an antiplatelet drug from Centocore). Examples of suitable antimitotic agents include methotrexate, azathioprine, vincristine, vinblastine, fluorouracil, adriamycin, and mitomycin. Examples of suitable cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck); calcium channel blockers (such as Nifedipine), colchicine, fibroblast growth factor (FGF) antagonists, fish oil (omega 3-fatty acid), histamine antagonist, LOVASTATIN (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Surmin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone.

FIGS. 4A–4B illustrate stent 10 in accordance with another embodiment of the present invention. In lieu of, or in addition to, coating outer surface 18 and inner surface 20 with polymeric coatings, cavities 34a and/or 34b are disposed in surfaces 18 and 20, respectively, for releasably containing the therapeutic and/or angiogenic substances. Cavities 34a within outer surface 18 contain a therapeutic substance, as indicated by dotted region 36, and cavities 34b within inner surface 20 contain an angiogenic substance, as indicated by dotted region 38. The substances can be deposited into the cavities in a solid form or contained in a polymeric matrix for reducing the rate of release.

Using the Embodiments of the Device to Treat Ischemia

FIGS. 5A–5D illustrate the use of stent 10 in a vessel 40 through which blood flows in a downstream direction 42. Vessel 40 is illustrated having an occlusion 44 and an ischemic region 46 downstream of occlusion 44. Referring to FIG. 5A, stent 10, carrying an angiogenic substance within a first coating on inner surface 20 and/or in cavities 34b within inner surface 20, is positioned within vessel 40 at a location that is upstream of, or proximal to, occlusion 44. In one such embodiment, stent 10 is made of a bioabsorbable material. As indicated by dashed arrows 48 in FIG. 5B, the angiogenic substance is released from inner surface 20 into blood flowing through central bore 22 in the downstream direction 42. The angiogenic substance, as illustrated by dotted region 38 in FIG. 5C, emerges from the distal end of stent 10, flowing in the downstream direction 42 toward and through occlusion 44.

Figure 5D:
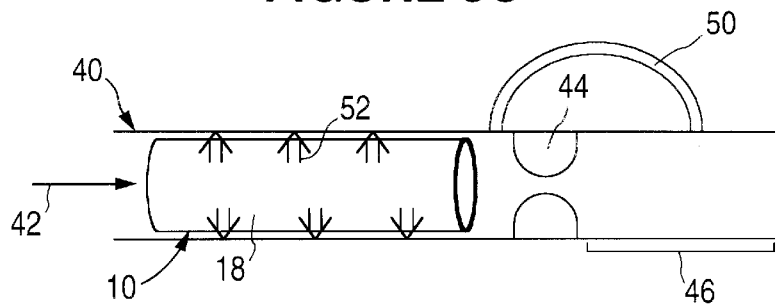

Referring to FIG. 5D, the released angiogenic substance can stimulate or promote formation of one or more collateral vessels 50 downstream of, or distal to, the site of implantation of stent 10. Such arteriogenesis enables circumvention of occlusion 44 by providing an alternate, less resistant pathway through which blood may travel. Accordingly, blood flow to ischemic region 46 is increased as blood travels through collateral vessel 50 as well as through occluded vessel 40.

The angiogenic substance can also stimulate angiogenesis downstream of the site of implantation of stent 10. Microvessels can provide blood with an increased number of pathways. Blood flow to ischemic region 46 can be therefore increased in primarily two ways. First, the increased number of pathways through which blood may flow can result in an increase in the amount of blood that reaches ischemic region 46. Second, an increased capillary bed in the ischemic region will allow more efficient distribution of blood in this zone and will result in a decreased overall resistance of this bed. Such a decrease in pressure may allow more blood to travel through vessel 40 due to a lower resistance therein.

Stent 10 can optionally provide for the release of a therapeutic substance carried within second coating 32 on outer surface 18 and/or in cavities 34a within outer surface 18, as illustrated by arrows 52. In an embodiment in which the therapeutic substance is a second angiogenic substance, the second angiogenic. substance can stimulate formation of additional collateral vessels 50 as well as additional microvessels. Alternatively, in an embodiment in which the therapeutic substance is a non-angiogenic substance, the therapeutic substance can otherwise act at the site of implantation of stent 10 for the treatment of vessel 40. By way of example, in an embodiment in which the therapeutic substance is an anti-proliferative substance, e.g., actinomycin D, the substance can help inhibit abnormal migration or proliferation of smooth muscle cells at the site at which stent 10 was implanted.

Figure 6:
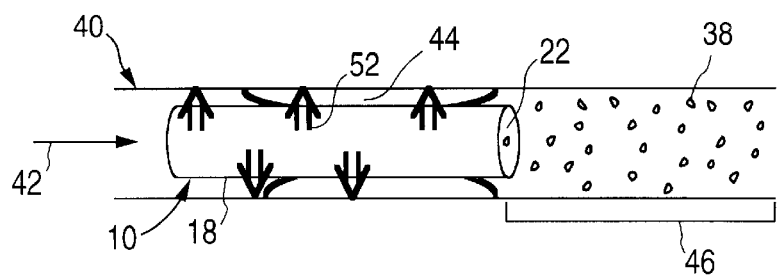
FIG. 6 illustrates a method for increasing blood flow to ischemic tissue in accordance with another embodiment of the present invention.

Referring to FIG. 6, stent 10 may be used to mechanically dilate vessel 40 in addition to providing treatment via the release of an angiogenic substance and an optional second therapeutic substance. Stent 10 can be positioned within vessel 40 such that stent 10 extends at least partially through occlusion 44. Stent 10 can physically hold open the wall of vessel 40 at the site of implantation. Accordingly, blood can flow more freely through the previously-occluded portion of vessel 40 in the downstream direction 42 toward ischemic region 46.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A stent, comprising:
   a tubular body having an outer surface configured to contact the wall of a vessel and an inner surface;
   a first coating supported by the inner surface and containing an angiogenic substance, the first coating configured to release the angiogenic substance in the vessel; and
   a second coating supported by the outer surface and containing a therapeutic substance capable of inhibiting migration or proliferation of smooth muscle cells, the second coating configured to apply the therapeutic substance to the wall of the vessel,
   wherein the outer surface is free from the first coating containing the angiogenic substance and the inner surface is free from the second coating containing the therapeutic substance.

2. The stent of claim 1, wherein the angiogenic substance is selected from a group of vascular endothelial growth factor, fibroblast growth factors, monocyte chemoattractant protein 1, transforming growth factor beta, transforming growth factor alpha, lipid factors, hypoxia-inducible factor 1-alpha, PR39, del 1, nicotine, insulin-like growth factors, placental growth factor, hepatocyte growth factor, estrogen, follistatin, proliferin, cytokines, tumor necrosis factor, erythropoietin, granulocyte colony-stimulating factor, granulocyte macrophage colony-stimulating factor, angiogenin, hormones, and genes that encode such substances.

3. The stent of claim 1, wherein the angiogenic substance is a vascular endothelial growth factor.

4. The stent of claim 1, wherein the angiogenic substance is a fibroblast growth factor.

5. The stent of claim 1, wherein the angiogenic substance is monocyte chemoattractant protein 1.

6. The stent of claim 1, wherein the angiogenic substance is a transforming growth factor beta.

7. The stent of claim 1, wherein the angiogenic substance is a transforming growth factor alpha.

8. The stent of claim 1, wherein the angiogenic substance is a lipid factor.

9. The stent of claim 1, wherein the angiogenic substance is hypoxia-inducible factor 1-alpha.

10. The stent of claim 1, wherein the angiogenic substance is PR39.

11. The stent of claim 1, wherein the angiogenic substance is del 1.

12. The stent of claim 1, wherein the angiogenic substance is nicotine.

13. The stent of claim 1, wherein the angiogenic substance is an insulin-like growth factor.

14. The stent of claim 1, wherein the angiogenic substance is a placental growth factor.

15. The stent of claim 1, wherein the angiogenic substance is a hepatocyte growth factor.

16. The stent of claim 1, wherein the angiogenic substance is estrogen.

17. The stent of claim 1, wherein the angiogenic substance is follistatin.

18. The stent of claim 1, wherein the angiogenic substance is proliferin.

19. The stent of claim 1, wherein the angiogenic substance is a cytokine.

20. The stent of claim 1, wherein the angiogenic substance is a tumor necrosis factor.

21. The stent of claim 1, wherein the angiogenic substance is erythopoietin.

22. The stent of claim 1, wherein the angiogenic substance is a granulocyte colony-stimulating factor.

23. The stent of claim 1, wherein the angiogenic substance is a granulocyte macrophage colony-stimulating factor.

24. The stent of claim 1, wherein the angiogenic substance is angiogenin.

25. A stent for implanting in a blood vessel comprising a tubular structure having an inner surface and an outer surface, comprising:
   a first therapeutic substance carried by the inner surface, the first therapeutic substance configured to be released downstream with the flow of blood; and
   a second therapeutic substance, different from the first therapeutic substance, the second therapeutic substance carried by the outer surface and configured to be delivered to the blood vessel wall,
   wherein the first therapeutic substance facilitates therapeutic angiogenesis and the second therapeutic substance inhibits migration or proliferation of smooth muscle cells,
   wherein the outer surface is free from the first therapeutic substance and wherein the inner surface is free from the second therapeutic substance.

26. The stent of claim 25, wherein the inner surface has a first polymeric coating deposited thereon for the sustained release of the first therapeutic substance and wherein the outer surface has a second polymeric coating deposited thereon for the sustained release of the second therapeutic substance.

27. The stent of claim 25, wherein the first therapeutic substance is selected from a group of vascular endothelial growth factor, fibroblast growth factors, monocyte chemoattractant protein 1, transforming growth factor beta, transforming growth factor alpha, lipid factors, hypoxia-inducible factor 1-alpha, PR39, del 1, nicotine, insulin-like growth factors, placental growth factor, hepatocyte growth factor, estrogen, follistatin, proliferin, cytokines, tumor necrosis factor, erythropoietin, granulocyte colony-stimulating factor, granulocyte macrophage colony-stimulating factor, angiogenin, hormones, and genes that encode such substances.

28. The stent of claim 25, wherein the second therapeutic substance is selected from a group of actinomycin D, docetaxel and paclitaxel.

* * * * *

UNITED STATES PATENT AND TRADEMARK OFFICE
CERTIFICATE OF CORRECTION

PATENT NO. : 6,660,034 B1
DATED : December 9, 2003
INVENTOR(S) : Mandrusov et al.

It is certified that error appears in the above-identified patent and that said Letters Patent is hereby corrected as shown below:

Column 3,
Line 44, change "FGF-1is 30-100 times" to -- FGF-1 is 30-100 times --.

Column 4,
Line 12, change "HIF-1-alpha MRNA" to -- HIF-1-alpha mRNA --.

Column 5,
Line 1, change "as wells as migration" to -- as well as migration --.

Column 10,
Line 38, change "erythopoietin" to -- erythropoietin --.

Column 12,
Line 5, change "ofactinomycin D" to -- of actinomycin D --.

Signed and Sealed this

Sixteenth Day of March, 2004

JON W. DUDAS
*Acting Director of the United States Patent and Trademark Office*